US009767550B2

(12) United States Patent
Carlsen et al.

(10) Patent No.: US 9,767,550 B2
(45) Date of Patent: Sep. 19, 2017

(54) METHOD AND DEVICE FOR ANALYSING A REGION OF INTEREST IN AN OBJECT USING X-RAYS

(75) Inventors: Ingwer-Curt Carlsen, Hamburg (DE); Thomas Koehler, Norderstedt (DE); Gerhard Martens, Henstedt-Ulzburg (DE); Ewald Rossl, Ellerau (DE); Rafael Wiemker, Kisdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 371 days.

(21) Appl. No.: 13/989,507

(22) PCT Filed: Dec. 5, 2011

(86) PCT No.: PCT/IB2011/055463
§ 371 (c)(1),
(2), (4) Date: May 24, 2013

(87) PCT Pub. No.: WO2012/080900
PCT Pub. Date: Jun. 21, 2012

(65) Prior Publication Data
US 2013/0236079 A1   Sep. 12, 2013

(30) Foreign Application Priority Data
Dec. 13, 2010   (EP) .................... 10194734

(51) Int. Cl.
G06K 9/00   (2006.01)
G06T 7/00   (2017.01)
G01N 23/04   (2006.01)

(52) U.S. Cl.
CPC ......... *G06T 7/0012* (2013.01); *G01N 23/046* (2013.01); *G01N 2223/419* (2013.01)

(58) Field of Classification Search
CPC ........ G06T 2207/30004; G06T 7/0079; G06K 9/0014
See application file for complete search history.

(56) References Cited

U.S. PATENT DOCUMENTS

| | | | |
|---|---|---|---|
| 7,920,673 B2* | 4/2011 | Lanza .................... | G02B 27/52 378/62 |
| 8,351,665 B2* | 1/2013 | Tearney ................ | A61B 10/02 382/128 |
| 2005/0018201 A1* | 1/2005 | de Boer ............... | A61B 5/0059 356/479 |
| 2007/0189590 A1* | 8/2007 | Fidrich et al. ................ | 382/128 |
| 2008/0097225 A1* | 4/2008 | Tearney ................ | A61B 18/22 600/478 |
| 2009/0192358 A1* | 7/2009 | Jaffer .................... | A61B 5/0066 600/182 |
| 2009/0196477 A1* | 8/2009 | Cense .................... | A61B 3/102 382/131 |
| 2009/0290156 A1* | 11/2009 | Popescu ............ | G01N 15/1434 356/338 |
| 2009/0316857 A1 | 12/2009 | David | |
| 2010/0002241 A1* | 1/2010 | Hirose ................... | A61B 3/102 356/497 |
| 2010/0086189 A1* | 4/2010 | Wang ........................ | G06T 5/00 382/132 |
| 2010/0177864 A1* | 7/2010 | Donath et al. .................. | 378/16 |
| 2012/0200694 A1* | 8/2012 | Garsha ............... | G01N 21/6456 348/79 |

FOREIGN PATENT DOCUMENTS

WO   WO2010109368   9/2010

OTHER PUBLICATIONS

Weitkamp et al., ANKAphase: software for single-distance phase retrieval from inline X-ray phase-contrast radiographs, 2011, J Synchrotron Radiat., pp. 617-629.*
F. Pfeiffer et al., "X-Ray Dark-Field and Phase-Contrast Imaging Using a Grating Interferometer", Journal of Applied Physics, American Institute of Physics, new York, US, vol. 105, No. 10, May 19, 2009, pp. 102006-1-102006-4.
F. Pfeiffer et al., "Hard-X-Ray Dark-Field Imaging Using a Grating Interferometer", Nature Materials, vol. 7, No. 2, Feb. 1, 2008, pp. 134-137.
M. Bech et al., "Advanced Contrast Modalities for X-Ray Radiology: Phase-Contrast and Dark-field Imaging using a Grating interferometer", Zietschrift fur Medizineische Physik, vol. 20, No. 1, Jan. 15, 2010, pp. 7-16.
M. Bech et al., "Quantitative X-Ray Dark-Field Computed Tomography; Quantitative X-Ray Dark-Field Computer Tomography", Physics in Medicine and biology, Taylor and Francis Ltd., London, GB, vol. 55, No. 18, Aug. 31, 2010, pp. 5529-5539.
K.G. Baum et al., "Fusion Viewer: A New Tool for Fusion and Visualization of Multimodal Medical Data Sets", Journal of Digital Imaging; the Journal of the Society for Computer Applications in Radiology, Springer-Verlag, NE, vol. 21, No. 1, Oct. 25, 2007, pp. 59-68.
ENDO: "Pancreatic Arteriovenous Malformation: A Case Report of Hemodynamic Analysis Using Multi-detector Row Computed Tomography and Post-Processing Methods", JOP. Journal of the Pancrease, vol. 10, No. 1, Jan. 1, 2009, pp. 59-63.
L. Rusko et al., "Automatic Segmentation of the Liver from Multi-and Single-Phase Contrast-Enhanced CT Images", Medical Image Analysis, Oxford University Press, Oxford, GB, vol. 13, No. 6, Dec. 1, 2009, pp. 871-882.
Haitham Shammaa M. et al., "Segmentation of Multi-Material CT Data of mechanical Parts for Extracting Boundary Surfaces", Computer Aided Design, Elsevier Publishers, BV, Barking, GB, vol. 42, No. 2, Feb. 1, 2010, pp. 118-128.

* cited by examiner

*Primary Examiner* — Jonathan S Lee

(57) ABSTRACT

A method and a device for analyzing a region of interest in an object is proposed. The method comprises: (a) providing measurement data by a differential phase contrast X-ray imaging system, and (b) analyzing characteristics of the object in the region of interest. Therein, the measurement data comprise a 2-dimensional or 3-dimensional set of pixels wherein for each pixel the measurement data comprises three types of image data spatially aligned with each other, including (i) absorption representing image data A, (ii) differential phase contrast representing image data D, and (iii) coherence representing image data C. The analyzing step is based, for each pixel, on a combination of at least two of information comprised in the absorption representing image data A and information comprised in the differential phase contrast representing image data D and information comprised in the coherence representing image data C.

21 Claims, No Drawings

METHOD AND DEVICE FOR ANALYSING A REGION OF INTEREST IN AN OBJECT USING X-RAYS

FIELD OF THE INVENTION

The present invention relates to a method and a device for analysing a region of interest in an object using X-rays. Furthermore, the invention relates to a computer program product adapted to perform such method as well as a computer-readable medium comprising the computer program product.

BACKGROUND OF THE INVENTION

X-ray imaging systems are conventionally used for examining objects of interest, particularly in medical applications. Recently, an improved X-ray imaging method referred to as grating-based differential phase-contrast imaging (DPCI) has been proposed by F. Pfeiffer et al., Phys. Rev. Lett. 98(10), 108105, 2007. An example of a differential phase-contrast imaging system is described in WO 2010/109368 A1.

SUMMARY OF THE INVENTION

There may be a need for an improved capability of analysing, such as e.g. segmenting or classifying, internal structures in an object of interest.

Such need may be met by the subject-matter of the independent claims. Embodiments of the invention are described in the dependent claims.

According to a first aspect of the present invention a method of analyzing a region of interest in an object is proposed. The method comprises: (a) providing measurement data by a differential phase contrast X-ray imaging system, and (b) analyzing characteristics of the object in the region of interest. Therein, the measurement data comprise a 2-dimensional or 3-dimensional set of pixels wherein for each pixel the measurement data comprises three types of image data spatially aligned with each other, including (i) absorption representing image data A, (ii) differential phase contrast representing image data D, and (iii) coherence representing image data C. The analyzing step is based, for each pixel, on a combination of at least two of information comprised in the absorption representing image data A and information comprised in the differential phase contrast representing image data D and information comprised in the coherence representing image data C. For example, it may be advantageous to base the analyzing step, for each pixel, on a combination of information comprised in the absorption representing image data A and information comprised in the differential phase contrast representing image data D.

A gist of the present invention lies in the recognition that taking into account e.g. both, information comprised in the absorption representing image data A and information comprised in the differential phase contrast representing image data D, the analysis of the measurement data will allow for higher quality and accuracy than basing the analysis on absorption representing image data only as is conventionally done. Particularly, in segmenting techniques, criteria for boundary detection are frequently based on gradients in an absorption image. As information about such gradients may be obtained with a high accuracy from the differential phase contrast representing image data D, additionally assessing these data for obtaining an analysis of the X-ray measurement data may improve the overall analysis result. The analysis results may be used e.g. in mammography, radiography and computed tomography systems.

Additionally, an indication on a reliability of an analyzing result may be provided for each pixel based on information comprised in the coherence representing image data C. In other words, the information about the loss of coherence, i.e. the increase of decoherence, of an X-ray beam having passed through the region of interest may be used to provide an indication on how reliable the information comprised in the absorption representing image data A and the differential phase contrast representing image data D is and thus how reliable the analysis results from these data may be assumed. Such information may be very valuable for a physician in planning and performing e.g. a surgical operation. Alternatively, it is possible to use the coherence representing image data C to provide other information. For example the decoherence can be caused by a strong preponderance of fibre structures like fibrin filaments in a direction parallel to the grating structures of the interferometer.

The analysis may comprise segmenting different subregions within the region of interest based on the combination of information comprised in the absorption representing image data A and information comprised in the differential phase contrast representing image data D. A segmented visualization of anatomical features within the region of interest may then be provided to an observer such as a physician.

The segmenting techniques may comprise surface rendering, volume rendering, maximum intensity projection, interactive refinement of a display, region growing, front propagation, level set segmentation or model-based segmentation.

The method may further comprise a step of adjusting of properties of rendered surfaces in terms of colour, reflectivity, specularity and/or transparency based on the combination of at least two of the information comprised in the absorption representing image data A and the information comprised in the differential phase contrast representing image data D and the information comprised in the coherence representing image data C. Therein, the different types of information sources comprised in the different image data sets A, D, C may be visualized in different manners such that a human viewer may easily distinguish the visualized information content of displayed rendered surfaces.

In an alternative approach, the method may further comprise adjusting of opacity functions in volume renders based on the combination of at least two of the information comprised in the absorption representing image data A and the information comprised in the differential phase contrast representing image data D and the information comprised in the coherence representing image data C. Again, a human viewer may get easy access to the visualized information content of displayed volumes.

In order to provide an additional information content to a viewer, the method may further comprise signaling of areas in which a predetermined quality requirement or accuracy requirement cannot be met. Such requirements may be imposed e.g. by a clinical target application. For example, after or while segmenting the portions of the region of interest, it may be determined based on respective information included in the differential phase contrast representing image data D and/or the coherence representing image data C whether a portion cannot or can only marginally meet predetermined quality requirements or accuracy requirements and, if so, the segmented surfaces of this portion may be visualized in a specific way such that the viewer may easily recognize the lack of quality/accuracy.

As a further option, the method may comprise adjusting a degree of freedom and/or a sensitivity of user interaction for an interactive refinement based on information included in the differential phase contrast representing image data D and/or the coherence representing image data C.

In a specific embodiment, the method may further comprise classifying sub-regions within the region of interest based on analysis results, i.e. based on information included in the differential phase contrast representing image data D and/or the coherence representing image data C. Such classification may be of high quality as the additional information comprised in the image data D and C may be used to refine structural information comprised in the absorption representing image data A and to give indication of the reliability of such information such that the refined structure may be analyzed to more reliably classify the sub-regions.

Finally, the method may further comprise selecting a minimum reliability based on requirements of a clinical application, and pre-computing at least one of segmentation results and classification results for different reliability levels.

According to a second aspect of the present invention, a device for analyzing a region of interest in an object is proposed. The device is adapted to perform the method explained above. Specifically, the device is adapted for: (a) acquiring measurement data from a differential phase contrast X-ray imaging system and (b) analyzing characteristics of the object in the region of interest for each pixel. Therein, the measurement data comprise a 2-dimensional or 3-dimensional set of pixels wherein for each pixel the measurement data comprises three types of image data spatially aligned with each other, including: (i) absorption representing image data A, (ii) differential phase contrast representing image data D, and (iii) coherence representing image data C. Therein, the analyzing step is performed based on a combination of at least two of the information comprised in the absorption representing image data A and the information comprised in the differential phase contrast representing image data D and the information comprised in the coherence representing image data C.

According to a third aspect of the present invention, a computer program product is proposed which is adapted to perform the method according the above first aspect when executed on a computer.

According to a fourth aspect of the present invention, a computer readable medium is proposed having stored thereon a computer program product according to the preceding third aspect.

These and other aspects of the invention will become more apparent from and elucidated with reference to the embodiments described hereinafter.

DETAILED DESCRIPTION OF EMBODIMENTS

In the following, multiple embodiments of analysing methods according to the invention will be explained.

Diagnosis as well as planning and monitoring of treatment of many diseases typically rely on the analysis of X-ray images to delineate anatomical entities such as organs or lesions and to classify anatomical abnormalities with respect to their texture or boundary shape. Conventional X-ray imaging is based on measuring the spatial distribution of the attenuation of incoherent X-rays in two or three dimensions using projection, tomosynthesis or tomographic techniques, respectively.

Use of coherent X-rays for imaging purposes measuring changes in phase has recently been proposed by Pfeiffer et al. This technique allows for the simultaneously acquisition of three images:

1. the conventional attenuation image, which may be called herein absorption representing image data A. This image is depicting a spatial distribution of a linear attenuation coefficient, i.e. in mathematical terms, the imaginary part of the refraction index, of the penetrated medium. In 2D, these data comprise line integrals of the linear attenuation $\mu$, whereas in 3D, the line integrals can usually be reconstructed such that the data comprises a map of the linear attenuation itself.

2. the gradient image which, in 2D, may be present in the form of gradients of the line-integrals of the X-ray refraction index decrement $\nabla\delta$ (related to the x-ray wave front's phase gradient) and which, in 3D, may be present in the form of a map of the X-ray refraction index decrement $\delta$ and which may be called herein differential phase contrast representing image data D. This image is representing an additional, new image depicting the phase gradient in the direction of coherence, i.e. in mathematical terms, the projection of the gradient of line-integrals of the real part of the refraction index onto the direction of coherence (perpendicular to the grating structures of the interferometer) in 2D, caused by the spatially varying X-ray refraction index of the penetrated medium, and 3. the de-coherence image which may present a quantitative measure $\epsilon$ of the loss of visibility upon transmission of the X-rays by the object and which may be called herein coherence representing image data C. This image is representing an additional, new image depicting the loss of coherence the original X-rays have undergone while penetrating the medium.

A problem addressed by this disclosure is the weak contrast between different types of soft tissue and the corresponding difficult differentiation in the absorption images. This can at least partially be overcome by including information from $\delta$ and $\epsilon$, i.e. the image data sets D and C, in the enhancement of low contrast edges or boundaries between structures.

In X-ray image analysis such as image segmentation, visualization and refinement of anatomical structures based on computerized image segmentation and classification of X-ray images, the robustness of segmentation algorithms strongly depends on the changes in signal value when crossing the boundary between two image regions. The less pronounced this difference becomes the more difficult it gets to draw a segmentation line between the two regions. This might be the case for example for a tumour region surrounded by healthy tissue on a conventional attenuation based image. A main idea put down in this disclosure is that the criteria for the boundary detection can be based not only on the gradients in the absorption image but also on the directly measured gradients of the x-ray refraction index decrement $\delta$.

In the following, different embodiments of boundary detection, image segmentation and other X-ray image analysis procedures are given in detail.

If a segmentation algorithm detects boundaries based on the condition that the absolute value of the image gradient in the attenuation image $|\nabla\mu|$ is larger than a predefined threshold T, i.e.:

$$|\nabla\mu|>T$$

but the image noise $\sigma$ is not sufficiently far from the difference in the average signal levels in the two regions $|\bar{\mu}_1-\bar{\mu}_2|$, i.e., the condition $$\frac{|\bar{\mu}_1 - \bar{\mu}_2|}{\sigma} \gg 1$$

is not satisfied well enough, the algorithm will hardly be able to identify the boundary between the regions to be segmented and noise will influence the segmentation results significantly.

In DPCI imaging, the gradient of the X-ray refraction index decrement $\nabla \delta$ is directly measured and might therefore provide a better measure for the detection of boundaries between two regions. Moreover, the gradient operation required for the attenuation image amplifies the noise present in the $\mu$ image and is not required for the phase gradient.

An alternative criterion for the detection of a boundary between two distinct regions might be based on a combination of all three measured quantities $\mu$, $\nabla \delta$, $\epsilon$, in a differential phase contrast setup, for example in the following form:

$$|\nabla \mu(x,y)| + \alpha f(\epsilon_{(x,y)})|(\nabla \delta)_M(x,y)| > T,$$

where the subscript M of the phase gradient is used to indicate that it is a directly measured quantity in contrast to the attenuation case where the gradient operator is explicitly applied to the measured quantity $\mu$. In the above equation it is made explicit the 2D spatial dependence of all measured quantities. As the loss of coherence in the x-ray phase, as reflected by an increase in $\epsilon$, is a measure for the reliability of the phase-gradient information, the function $f$ must a be monotonically decreasing function of its argument in order to serve as an appropriate weighting function for the importance of the phase-gradient for finding the boundary. The quantity a allows to adjust for an appropriate absolute balance between the two terms and will mainly be determined by the noise and contrast levels in the original measurements $\mu$, $\nabla \delta$.

In another realization, the three measured quantities could also be used to enhance edges by combining the information contained in the quantities $\mu$ and $\nabla \delta$, with $\epsilon$ as a control parameter regulating the degree to which the gradient information from and $\nabla \delta$ is used to enhance edges in $\mu$.

In still another realization, similar methods can be used to enhance edges in reconstructed tomographic images, where the noise power spectra of the reconstructed attenuation $\mu$ and energy-density images $\delta$ will be very different due to the different nature of the measured raw data.

The combined gradient from $\mu$, $\nabla \delta$, $\epsilon$ can be used not only in gradient-threshold-based segmentation algorithms, but also in all sorts of segmentations algorithms which make use of an edge-goodness-function for each pixel (increasing with the gradient magnitude), or a path-cost-function for each pixel (decreasing with the gradient magnitude). In all these segmentation algorithms (e.g. shortest path algorithms, graph-cut algorithms, region-growing algorithms, etc), the normal gradient is then replaced by the combined gradient, i.e. from $\mu$, $\nabla \delta$, $\epsilon$.

Any segmentation or pattern recognition method whose operation relies on intensity-based criteria controlling the inner working of the algorithm is a candidate to benefit from the incorporation of a combined analysis of at least two of the above three input image data sets A, D and C.

The following briefly describes four embodiments of computerized analysis of phase-contrast X-ray images for frequently used segmentation methods:

Region growing: Region growing techniques segment an image into regions showing similar intensity characteristics. Starting from one or more seed points, regions are grown by merging with picture elements provided their intensity characteristics are sufficiently similar to those of the region. In this way the region is extended until either no more sufficiently similar picture elements are found or some size or shape limit is reached. The merging as well as the limiting criteria can be refined in terms of intensity resolution using the information of the gradient image, i.e. by using higher grey-value resolution when neighboring picture elements are very similar and located in areas of well preserved X-ray coherence. This information is crucial when achieving reliable segmentation is imperative in areas were clinically relevant anatomical structures are located in close proximity, but differ in minute intensity values only, e.g. CT images of the abdomen. Using the decoherence information, the reliability of the derived segmentation results can be marked and areas not meeting quality requirements demanded by the target application can be signaled, e.g. by using color overlays of graphical symbols, to guide the clinicians attention to these areas as areas demanding further scrutiny from a clinical point of view.

Front propagation: Front propagation techniques segment an image by simulating the propagation of wave fronts. The wave front iteratively progresses in fixed time intervals with the propagation speed being determined by intensity characteristics of the image areas the wave is transpassing. Diminishing the speeds along significant intensity gradients, the wave propagation is brought to a stand-still indicating the final result of the segmentation procedure. The speed function can be fine tuned according to the high-resolution intensity gradient image information to accurately navigate the wave front through areas of good X-ray coherence, i.e. high-quality intensity information. Areas of low quality gradient information may either be avoided or rapidly progressed according to the quality requirements of the target application. As above, areas where segmentation accuracy is limited can be marked and signaled to the clinical user.

Level Set segmentation: Level set methods are closely related to front propagation. The same wave equations are used, however, wave propagation is allowed to occur also backward in time. In this way, segmentation results can be iteratively refined when errors occur, e.g. violating some shape or size limits, penetrating into neighboring segments etc. Detecting such segmentation errors as well as controlling the reverse propagation can be fine tuned using the gradient image and the decoherence image, controlling e.g. the inclusion or exclusion of areas of strongly deteriorating coherence, sensitizing wave propagation to high-resolution attenuation gradients with progressing iteration etc.

Model-based segmentation: Here an anatomical model describing location, size, shape, contrast etc. of an anatomical entity is instantiated and adjusted to the anatomy of the patient of interest. This adjustment is controlled by two functions—a force term that tries to align the anatomy as accurately as possible with significant intensity changes encountered in the image and a regularizing term that prevents the model from wiggling too strongly about structural noise. The gradient image and the quality image are helpful in fine tuning these crucial terms, e.g. adjusting model rigidity with grade of coherence to continue a model smoothly through areas of unreliable intensity information where the model otherwise might get trapped by structural noise. Similarly and depending on the clinical question at hand, the force term can be fine tuned to sensitize the model to minute, but clinically relevant intensity changes to separate tumor boundaries from neighboring critical organs, but doing so only in areas where such minute changes can be detected reliably.

The four embodiments may suffice to illustrate the effect phase contrast imaging may have on intensity-based segmentation of medical images.

The following briefly describes some embodiments of phase-contrast adjusted surface or volume rendering techniques:

Surface rendering: Surface rendering techniques are based on computer representations of the surfaces of segmented objects, in the simplest form e.g. iso-surfaces of equal intensity values. The display of these surfaces is generated according to some shading model describing the local colour, reflectivity, specularity and transparency of the surface and some lighting model describing the distribution of the light, ambient light and scattering properties of the surrounding medium. Shading and lighting models can be adjusted in accordance with the information acquired during phase contrast X-ray imaging. Small scale surface structures derived from the gradient data can be enhanced in areas of well preserved X-ray coherence by increasing reflectivity and specularity over the respective surface areas to turn such fine-scale structure more conspicuous. Similarly, the surface display can be given a more diffuse or fuzzy appearance in areas where segmented surface elements are of less reliability as indicated e.g. by deteriorated X-ray coherence. Similarly the surface colour can be adjusted to signal areas for which the clinically demanded precision requirements could not be met as determined from the gradient and coherence information. If these areas coincide with areas of proximity of critical anatomical entities, e.g. to tell a tumour from neighbouring vasculature or organ at risk, the transparency of the respective surfaces can be adjusted to provide a simultaneous view onto the neighbouring entities.

Volume rendering: Volume rendering techniques generate visual representations of objects that defy the definition of unambiguous surfaces. The three-dimensional distribution of the original intensity values or (often fuzzy) membership values are not subjected to segmentation procedures, but are directly rendered into displays using opacity functions. These opacity functions define in which way the intensity values encountered along rays cast through the three-dimensional data set along the viewing direction are integrated into the two-dimensional viewing plane. Integrating the gradient and decoherence information into the opacity functions allows to augment the resulting display. Over volume areas of well preserved phase coherence, i.e. reliable phase gradient information, opacity functions can be turned sensitive to small scale variations of the attenuation data to turn minute details more conspicuous in the final display. Similarly the transparency ($\alpha$-channel) can be adjusted to give simultaneous view to neighbouring structures over such areas where fine anatomical details can be reliably resolved to clarify complex proximity relations, e.g. to tell a tumour from neighbouring vasculature or to display the infiltration of an organ at risk by a tumour entity. The RGB-channels can be adjusted in accordance with the decoherence information to signal areas of insufficiently rendered anatomy using colouring or fuzziness to give the clinical used immediate feedback on areas demanding further scrutiny and refined interactively controlled analysis.

Maximum intensity projections: Volume renderings of special importance in medical applications are maximum intensity projections generated by displaying the maximum intensity value encountered along rays cast through the three-dimensional data set along the viewing direction. This technique is frequently used to display vascular structures to examine vascular malformations as well as the vascularity inside and outside of organs or tumours. Small scale vascular structures can be resolved over areas of well-preserved phase coherence by integrating small scale gradient information into the refined analysis of the intensity distribution in the proximity of maximal intensity values. In combination with rotations about an axis orthogonal to the direction of coherence, the display can be updated accordingly in support of improved visual analysis of complex vascular structures.

Interactive refinement of the display: Generating clinically acceptable visual representations of three-dimensional anatomies requires the simultaneous manipulation of a fairly large number of parameters controlling the underlying surface or volume rendering techniques. The number of degrees of freedom involved often turns this task time consuming and frustrating to the user especially when it is hard to predict the outcome of these manipulations. Using the phase gradient and decoherence information, smart presets of these parameters can be defined, e.g. to augment the display over areas of well preserved X-ray coherence and associated gradient information. Similarly, the sensitivity of interaction can be adjusted in accordance with the available gradient and coherence data to prevent the user from driving the system off well-defined displays too easily or erroneously.

These four embodiments may suffice to illustrate the effect phase contrast imaging may have on improved visual representation anatomical entities on the base of X-ray data.

It may be noted that the described methods may be performed by a computer. Accordingly, an embodiment of the present invention relates to a computer program product or a computer program element which is characterized by being adapted to perform or control respective method steps of the described method according to embodiments of the invention when executed on a computer. The computer program product might therefore be stored on a computer unit which may be adapted to perform or induce a performing of the method steps. Moreover, it may be adapted to operate components of the above-described device. The computing device may be adapted to operate automatically and/or to execute the orders of a user. The computer program product will be loaded into a working memory of a data processor. The data processor may thus be equipped to carry out the method according to embodiments of the invention. This embodiment of the invention covers both, a computer program product that right from the beginning uses the invention as well as a computer program product that by means of an up-date turns an existing program into a program that uses the invention. A computer-readable medium having stored thereon such computer program product may be provided for example as a CD-ROM. Alternatively, the computer program may also be provided over a network like the WorldWideWeb and can be downloaded into the working memory of the data processor. Accordingly, the computer-readable medium according to an embodiment may also be a medium for making the computer program product available for downloading.

It has to be noted that embodiments of the present invention are described herein with reference to different subject-matters. In particular, some embodiments are described with reference to method type claims whereas other embodiments are described with reference to device type claims. However, a person skilled in the art will gather from the above and the following description that, unless other notified, in addition to any combination of features belonging to one type of subject-matter also any combination between features relating to different subject-matters is considered to be disclosed with this application. However, all features can be combined providing synergetic effects that are more than the simple summation of the features.

In the claims and the specification, the word "comprising" does not exclude other elements or steps, and the indefinite article "a" does not exclude a plurality. It should also be noted that reference signs in the claims should not be construed as limiting the scope of the claims.

The invention claimed is:

1. A method of analyzing a region of interest in an object, the method comprising:
   providing measurement data by a differential phase contrast X-ray imaging system, the measurement data comprising an at least 2-dimensional set of pixels wherein for each pixel the measurement data comprises three types of image data spatially aligned with each other, including:
      absorption representing image data A,
      differential phase contrast representing image data D, and
      coherence representing image data C;
   analyzing characteristics of the object in the region of interest based, for each pixel, on a combination of at least two of information comprised in the absorption representing image data A and information comprised in the differential phase contrast representing image data D and information comprised in the coherence representing image data C; and
   providing for each pixel an indication on a reliability of an analyzing result based on information comprised in the coherence representing image data C.

2. The method of claim 1, wherein the analysis comprises segmenting different sub-regions within the region of interest based on the combination of information comprised in the absorption representing image data A and information comprised in the differential phase contrast representing image data D.

3. The method of claim 1, the method further comprising:
   performing surface rendering that forms a rendered surface; and
   adjusting of properties of said rendered surface in terms of at least one of color, reflectivity, specularity and transparency based on the combination of at least two of information comprised in the absorption representing image data A and information comprised in the differential phase contrast representing image data D and information comprised in the coherence representing image data C.

4. A device for analyzing a region of interest in an object, the device comprising:
   a differential phase contrast X-ray imaging system comprises an interferometer that includes grating structures for differential phase contrast X-ray imaging; and
   a data processor adapted for:
      acquiring measurement data from said differential phase contrast X-ray imaging system, the measurement data comprising an at least 2-dimensional set of pixels wherein for each pixel the measurement data comprises three types of image data spatially aligned with each other, including:
         absorption representing image data A,
         differential phase contrast representing image data D, and
         coherence representing image data C;
      analyzing characteristics of the object in the region of interest for each pixel based on a combination of at least two of information comprised in the absorption representing image data A and information comprised in the differential phase contrast representing image data D and information comprised in the coherence representing image data C; and
      providing for each pixel an indication on a reliability of an analyzing result based on information comprised in the coherence representing image data C.

5. The device of claim 4, wherein the analysis comprises segmenting different sub-regions within the region of interest based on the combination of information comprised in the absorption representing image data A and information comprised in the differential phase contrast representing image data D, and wherein the segmenting techniques comprise at least one of region growing, front propagation, level set segmentation and model-based segmentation.

6. The device of claim 4, wherein said data processor is further adapted for selecting a minimum reliability based on requirements of a clinical application, and pre-computing at least one of segmentation results and classification results for different reliability levels.

7. The device of claim 4, from among said at least two there being said information comprised in the coherence representing image data C.

8. The device of claim 4, from among said at least two there being said information comprised in the differential phase contrast representing image data D.

9. The device of claim 4, configured to utilize the pixel-specific analyzing to enhance an intensity-based criterion.

10. The device of claim 9, configured to use the enhanced criterion in controlling inner workings of at least one of an image segmentation algorithm and a pattern recognition algorithm.

11. The device of claim 4, configured to use the pixel-specific analyzing to form, based on the combination, a metric for the pixel and to utilize said metric in image segmentation.

12. The device of claim 11, wherein the utilizing of said metric comprises thresholding said metric.

13. The device of claim 4, configured for enhancing edges based on a result of the combining.

14. The device of claim 4, wherein said data processor is further adapted for using the indication of reliability in at least one of edge enhancement and image segmentation.

15. A non-transitory computer readable medium embodying a program for analyzing a region of interest in an object, said program having instructions executable by a processor for performing a plurality of acts, from among said plurality there being the acts of:
   providing measurement data by a differential phase contrast X-ray imaging system, the measurement data comprising an at least 2-dimensional set of pixels wherein for each pixel the measurement data comprises three types of image data spatially aligned with each other, including:
      absorption representing image data A,
      differential phase contrast representing image data D, and
      coherence representing image data C;
   analyzing characteristics of the object in the region of interest based, for each pixel, on a combination of at least two of information comprised in the absorption representing image data A and information comprised in the differential phase contrast representing image data D and information comprised in the coherence representing image data C; and
   using the pixel-specific analyzing to form, based on the combination, a metric for the pixel and utilizing said metric in image segmentation, wherein said utilizing comprises thresholding said metric.

16. The computer readable medium of claim 15, wherein from among said plurality there is the further act of adjusting of opacity functions in volume renders based on the combination of at least two of information comprised in the absorption representing image data A and information comprised in the differential phase contrast representing image data D and information comprised in the coherence representing image data C.

17. The computer readable medium of claim 15, wherein from among said plurality there is the further act of distinguishing a portion of said object in which a predetermined quality requirement cannot be met from a part of said object in which said requirement can be met and signaling said portion, said portion being less than said object as a whole, wherein said distinguishing includes deciding, by said processor, that said predetermined quality cannot be met and that said predetermined quality can be met.

18. The computer readable medium of claim 17, wherein said distinguishing is based on at least one of the differential phase contrast representing image data D and the coherence representing image data C.

19. The computer readable medium of claim 15, wherein from among said plurality there is the further act of adjusting, in connection with an interactive refinement of a display, at least one of a degree of freedom and a sensitivity of user interaction for said interactive refinement.

20. The computer readable medium of claim 15, wherein from among said plurality there is the further act of providing for each pixel an indication on a reliability of an analyzing result based on information comprised in the coherence representing image data C.

21. A device for analyzing a region of interest in an object, said device comprising:
a differential phase contrast X-ray imaging system that comprises an interferometer that includes grating structures for differential phase contrast X-ray imaging; and
a data processor adapted for:
acquiring measurement data from a differential phase contrast X-ray imaging system, the measurement data comprising an at least 2-dimensional set of pixels wherein for each pixel the measurement data comprises three types of image data spatially aligned with each other, including:
absorption representing image data A,
differential phase contrast representing image data D, and
coherence representing image data C;
analyzing characteristics of the object in the region of interest for each pixel based on a combination of at least two of information comprised in the absorption representing image data A and information comprised in the differential phase contrast representing image data D and information comprised in the coherence representing image data C; and
adjusting, based on the combination, at least one of: a) properties of rendered surfaces in terms of at least one of color, reflectivity, specularity and transparency; and b) opacity functions in volume renders.

* * * * *